(12) United States Patent
Ando

(10) Patent No.: US 10,815,198 B2
(45) Date of Patent: Oct. 27, 2020

(54) METHOD FOR SEPARATING AND PURIFYING 2-CHLORO-3-TRIFLUOROMETHYLPYRIDINE

(71) Applicant: ISHIHARA SANGYO KAISHA, LTD., Osaka (JP)

(72) Inventor: Takayoshi Ando, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 16/531,925

(22) Filed: Aug. 5, 2019

(65) Prior Publication Data
US 2020/0048202 A1    Feb. 13, 2020

(30) Foreign Application Priority Data
Aug. 7, 2018 (JP) .................. 2018-148607

(51) Int. Cl.
*C07D 213/26* (2006.01)
(52) U.S. Cl.
CPC ........ *C07D 213/26* (2013.01); *C07B 2200/13* (2013.01)
(58) Field of Classification Search
CPC .................... C07D 213/26; C07B 2200/13
USPC ....................................................... 546/346
See application file for complete search history.

(56) References Cited

FOREIGN PATENT DOCUMENTS

| CN | 101062915 A | 10/2007 |
|----|-------------|---------|
| EP | 0 013 474 A2 | 7/1980 |
| GB | 2 045 245 A | 10/1980 |
| GB | 2 045 761 A | 11/1980 |
| JP | 55-122762 A | 9/1980 |
| JP | 55-124762 A | 9/1980 |
| JP | 55-147261 A | 11/1980 |
| JP | 56-100764 A | 8/1981 |
| JP | 56-120667 A | 9/1981 |

OTHER PUBLICATIONS

T.P. Hilditch, Catalytic Processes in Applied Chemistry, D. Van Nostrand Co., New York 1929, p. Xiii-XV (3 pages) (Year: 1929).*
Communication dated Oct. 9, 2019, issued by the European Patent Office in corresponding European Application No. 19190480.4.

* cited by examiner

*Primary Examiner* — Taylor V Oh
(74) *Attorney, Agent, or Firm* — Sughrue Mion, PLLC

(57) ABSTRACT

A method for separating and purifying 2-chloro-3-trifluoromethylpyridine useful as an intermediate for medicines, agrochemicals, and the like is provided.

The method includes:

1) in the process of producing chloro β-trifluoromethylpyridine compounds by allowing a β-methylpyridine compound to react with chlorine and hydrogen fluoride in a reaction apparatus, allowing a β-trifluoromethylpyridine compound to react with chlorine in a reaction apparatus, or allowing a chloro β-trichloromethylpyridine compound to react with hydrogen fluoride in a reaction apparatus, 2) fractionating a liquid mixture containing chloro β-trifluoromethylpyridine compounds from the reaction apparatus, and 3) separating and purifying 2-chloro-3-trifluoromethylpyridine from the liquid mixture.

5 Claims, No Drawings

METHOD FOR SEPARATING AND PURIFYING 2-CHLORO-3-TRIFLUOROMETHYLPYRIDINE

TECHNICAL FIELD

The present invention relates to a method for separating and purifying 2-chloro-3-trifluoromethylpyridine useful as an intermediate for medicines, agrochemicals, and the like.

BACKGROUND ART

Patent Documents 1 and 2 disclose a method for producing chloro β-trifluoromethylpyridine compounds characterized by allowing a β-methylpyridine compound to react with chlorine and anhydrous hydrogen fluoride in a vapor phase in the presence of a specific catalyst and an inert diluent. Examples thereof show, as the chloro β-trifluoromethylpyridine compounds, 2-chloro-5-trifluoromethylpyridine (hereinafter also referred to as 2,5-CTF) is mainly obtained and 2-chloro-3-trifluoromethylpyridine (hereinafter also referred to as 2,3-CTF), 2,6-dichloro-3-trifluoromethylpyridine (hereinafter also referred to as 2,3,6-DCTF), and the like are together obtained.

Patent Document 3 discloses a method for producing chloro 3-trifluoromethylpyridine compounds by chlorinating 3-trifluoromethylpyridine in the presence of an inert diluent. Examples thereof show, as the chloro β-trifluoromethylpyridine compounds, 2,5-CTF is mainly obtained and 2,3-CTF, 2,3,6-DCTF, and the like are together obtained.

Patent Documents 4 and 5 disclose a method for producing chloro β-trifluoromethylpyridine compounds characterized by allowing a β-trichloromethylpyridine compound to react with anhydrous hydrogen fluoride in a vapor phase in the presence of a specific catalyst. In Examples thereof, it is shown that, as the chloro β-trifluoromethylpyridine compounds, 2,5-CTF is mainly obtained.

RELATED ART

Patent Document

Patent Document 1: JP-A-55-147261
Patent Document 2: JP-A-56-120667
Patent Document 3: JP-A-55-122762
Patent Document 4: JP-A-55-124762
Patent Document 5: JP-A-56-100764

SUMMARY OF INVENTION

Problems to be Solved by the Invention

Both of 2,5-CTF and 2,3-CTF are useful compounds as e.g., intermediates of agrochemicals. However the production amount of 2,3-CTF is slight in the methods disclosed in Patent Documents 1 to 5. Though it may be considered to adopt another production method for producing 2,3-CTF in a high yield, if 2,3-CTF can be produced in the sufficient amount while 2,5-CTF is produced in a high yield, a high merit in cost is provided.

Means for Solving the Problems

As a result of investigations for solving the above problems, the present inventors have found a method for producing 2,3-CTF in a high yield and in good efficiency in cost by using a β-methylpyridine compound, a β-trifluoromethylpyridine compound, chloro β-trichloromethylpyridine compounds, and the like as raw materials, obtaining 2,5-CTF as a main product, and purifying 2,3-CTF from a distillation product fractionated in a distillation process by a simple method, and they have accomplished the present invention.

That is, the present invention provides a method (hereinafter also referred to as the method of the present invention) comprising:

1) in the process of producing chloro β-trifluoromethylpyridine compounds by allowing a β-methylpyridine compound to react with chlorine and hydrogen fluoride in a reaction apparatus, allowing a β-trifluoromethylpyridine compound to react with chlorine in a reaction apparatus, or allowing a chloro β-trichloromethylpyridine compound to react with hydrogen fluoride in a reaction apparatus, 2) fractionating a liquid mixture containing chloro β-trifluoromethylpyridine compounds from the reaction apparatus, and 3) separating and purifying 2-chloro-3-trifluoromethylpyridine from the liquid mixture.

Effects of the Invention

Based on the method of the present invention, 2-chloro-3-trifluoromethylpyridine useful as an intermediate for medicines, agrochemicals, and the like can be produced in a high yield and in high purity with good cost efficiency.

Embodiments for Carrying Out the Invention

The method of the present invention is performed as follows.

(1) Chloro β-trifluoromethylpridine compounds are produced by the methods shown in the following Reaction 1 to Reaction 3.

(Reaction 1) As shown in the following reaction formula, a β-methylpyridine compound represented by the formula (I) is allowed to react with chlorine and anhydrous hydrogen fluoride in a vapor phase in the presence of a catalyst and an inert diluent in a reaction apparatus to produce chloro β-trifluoromethylpyridine compounds represented by the formula (II). Then a liquid mixture containing chloro β-trifluoromethylpyridine compounds represented by the formula (II) is fractionated from the reaction apparatus by a distillation operation. The liquid mixture generally contains 2-chloro-5-trifluoromethylpyridine (2,5-CTF), 2-chloro-3-trifluoromethylpyridine (2,3-CTF), 2,6-dichloro-3-trifluoromethylpyridine (2,3,6-DCTF), and the like.

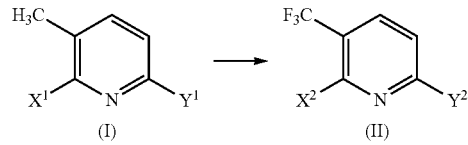

where $X^1$, $X^2$, $Y^1$ and $Y^2$ are a hydrogen atom or a chlorine atom independently, provided that at least one of $X^2$ and $Y^2$ is a chlorine atom.

The above Reaction 1 is a reaction in which the chloro β-trifluoromethylpyridine compounds represented by the formula (II) are produced by allowing a β-methylpyridine compound represented by the formula (I) to react with chlorine and anhydrous hydrogen fluoride in a vapor phase in the presence of a catalyst and an inert diluent.

Examples of the β-methylpyridine compound represented by the formula (I) used in the above Reaction 1 include β-picoline and a chloro β-picoline such as 2-chloro β-picoline, 6-chloro-β-picoline and 2,6-dichloro-β-picoline. In particular, β-picoline is easily available as a raw material for various organic synthetic chemical industries and the present invention is advantageous because the chloro β-trifluoromethylpyridine compounds can be directly produced from the compound.

Examples of the catalyst used in the above Reaction 1 include fluorides of a metal. Specific examples thereof include fluorides of aluminum, chromium, iron, cobalt and manganese. More specific examples thereof include hydrated aluminum trifluoride ($AlF_3.3H_2O$), aluminum trifluoride ($AlF_3$), chromium difluoride ($CrF_2$), hydrated chromium trifluoride ($CrF_3.3H_2O$), chromium trifluoride ($CrF_3$), chromium tetrafluoride ($CrF_4$), hydrated ferrous fluoride ($FeF_2.8H_2O$), ferrous fluoride ($FeF_2$), ferric fluoride ($FeF_3$), nickel(II) fluoride ($NiF_2$), hydrated nickel(II) fluoride ($NiF_2.3H_2O$), nickel(III) fluoride ($NiF_3$), cobalt(II) fluoride ($CoF_2$), cobalt(III) fluoride ($CoF_3$), manganese(II) fluoride ($MnF_2$), manganese(III) fluoride ($MnF_3$) and manganese tetrafluoride ($MnF_4$). The use amount of the catalyst is not categorically determined as it depends on the reaction conditions, but may be from 0.001 to 3 mol, desirably from 0.01 to 3 mol in terms of 1 mol of the raw material β-methylpyridine compound. Usually, the catalyst is mixed with a carrier such as active carbon, active alumina or aluminum trifluoride and allowed to be present as a fixed bed or a fluidized bed after molded into an appropriate-size particles or pellets. Moreover, the catalyst may be directly charged into a reaction tube in the form of a fluoride of the metal element, and allowed to be present, but it is industrially advantageous to use a method in which the metal element is charged into a reaction tube in the form of an oxide, a chloride or a carbonate salt or in the form of a hydrate of the above fluoride and is allowed to react with anhydrous hydrogen fluoride to be converted into a fluoride, thereby the catalyst being allowed to be present. For example, the reaction can be performed after a molded product of an oxide or chloride of the above metal element, such as chromium trioxide, ferric chloride or nickel oxide supported on an alumina carrier, is charged into a reaction tube and anhydrous hydrogen fluoride is introduced in advance, and they are allowed to react at 200 to 600° C. to convert the metal element into a fluoride thereof.

As the inert diluent, organic solvent of halogenated hydrocarbons such as carbon tetrachloride, chloroform, methylene chloride, F-112 ($CFCl_2.CFCl_2$) and F-113 ($CF_2Cl.CFCl_2$) and inert gases such as nitrogen, helium and argon can be used. These inert diluents have a function of suppressing combustion, carbonization, formation of tar-like by-products and the like.

At the time of carrying out the above Reaction 1, the raw materials and the inert diluent can be separately supplied into a reactor or they can be supplied in a mixed state thereof. Alternatively, they can be supplied simultaneously or sequentially or can be supplied at once or portionwise. For example, a mixture of the β-methylpyridine compound and the inert diluent or a mixture of chlorine and anhydrous hydrogen fluoride is separately supplied.

The use amounts of chlorine and anhydrous hydrogen fluoride are not categorically determined as it depends on the kind of the raw material β-methylpyridine compound, the kind of the objective compound, and the reaction apparatus. However, in general, chlorine is from 2 to 15 mol and anhydrous hydrogen fluoride is from 2 to 60 mol per 1 mol of the raw material β-methylpyridine compound, and the use amount of the inert diluent is from 2 to 70 mol per 1 mol of the raw material β-methylpyridine compound. The reaction temperature is from 300 to 600° C. and the residence time of the reaction mixture in the reaction zone is from 0.5 to 60 seconds, desirably from 3 to 60 seconds.

Usually, a fluorinated product containing chloro β-trifluoromethylpyridine compounds as main components, unreacted hydrogen fluoride and chlorine, intermediate products, hydrogen chloride as a by-product, and further a gaseous substance containing the inert diluent are discharged from the reaction apparatus, and the chloro β-trifluoromethylpyridine compounds are collected as a liquid mixture through an appropriate cooling and condensing apparatus. The liquid mixture generally contains 2,5-CTF, 2,3-CTF and 2,3,6-DCTF and the chloro β-trifluoromethylpyridine compounds are obtained, for example, in a formation rate of 85% or more. When intermediate products which do not reach formation of chloro β-trifluoromethylpyridine compounds in the collected liquid mixture, these intermediate products can be separated and recovered together with unreacted raw materials or inert diluent and can be recycled to the reaction zone.

Moreover, the above Reaction 1 can be conducted according to the description in JP-A-55-147261 and JP-A-56-120667.

(Reaction 2) As shown in the following reaction formula, a β-trifluoromethylpyridine compound represented by the formula (III) is allowed to react with chlorine in a vapor or liquid phase in a reaction apparatus to produce chloro β-trifluoromethylpyridine compounds represented by the formula (II). Then a liquid mixture containing chloro β-trifluoromethylpyridine compounds represented by the formula (II) is fractionated from the reaction apparatus by a distillation operation. The liquid mixture generally contains 2,5-CTF, 2,3-CTF, 2,3,6-DCTF, and the like.

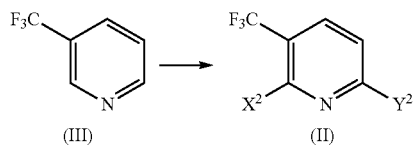

where $X^2$ and $Y^2$ are a hydrogen atom or a chlorine atom independently, provided that at least one of $X^2$ and $Y^2$ is a chlorine atom.

One embodiment of the above Reaction 2 is a reaction in which chloro β-trifluoromethylpyridine compounds represented by the formula (II) are produced by chlorinating a β-trifluoromethylpyridine compound represented by the formula (III) in a vapor phase in the presence of an inert diluent.

In general, the β-trifluoromethylpyridine compound and chlorine are separately introduced into the reaction apparatus with the inert diluent as a carrier and are subjected to the reaction. The inert diluents have a function of suppressing combustion, carbonization, formation of tar-like by-products and the like as in the case of a usual vapor-phase chlorination reaction, and specific examples thereof include inert gases such as nitrogen and helium, halogenated hydrocarbons such as carbon tetrachloride, trichloroethylene, tetrachloroethylene and tetrachlorodifluoroethane, and the like. However, industrially, nitrogen, carbon tetrachloride or a mixture thereof is desirably used. The use amounts of the inert diluent and chlorine are not categorically determined as it depends on the difference in the other reaction conditions.

However, in general, the inert diluent is from 3 to 70 mol, desirably from 10 to 20 mol and chlorine is from 0.5 to 5 mol, desirably from 0.8 to 3 mol per 1 mol of the β-trifluoromethylpyridine compound. The reaction temperature is from 270 to 500° C., desirably from 350 to 450° C. and the residence time of the reaction mixture in the reaction zone is from 0.5 to 60 seconds, desirably from 1 to 20 seconds.

The above Reaction 2 can be carried out, if desired, in the presence of a packing material such as a porous substance such as silica, alumina or silicon carbide, porcelain, a glass ball, or a mixture thereof. At the time of industrially carrying out the reaction, reaction efficiency can be improved by allowing the packing material to be present in the reactor as a fixed bed or a fluidized bed. The β-trifluoromethylpyridine compound, chlorine, and the inert diluent are commonly supplied into the reaction apparatus after preheating. At the time of supplying the β-trifluoromethylpyridine compound, it can be supplied after vaporization by introducing it into a high-temperature gaseous inert diluent or heating a solution obtained by dissolving it in a liquid inert diluent. In the reaction apparatus, predetermined reaction conditions are maintained and a desired reaction is carried out to produce the chloro β-trifluoromethylpyridine compounds.

Usually, a gaseous substance containing the chloro β-trifluoromethylpyridine compounds, the inert diluent, unreacted chlorine, and the like is discharged from the reaction apparatus, and the chloro β-trifluoromethylpyridine compounds are collected as a liquid mixture through an appropriate cooling and condensing apparatus. The liquid mixture generally contains 2,5-CTF, 2,3-CTF and 2,3,6-DCTF. When intermediate products, which do not reach formation of chloro β-trifluoromethylpyridine compounds are contained in the liquid mixture, these intermediate products can be separated and recovered together with unreacted raw materials or inert diluent and can be recycled to the reaction zone.

Another embodiment of the above Reaction 2 is a reaction in which chloro β-trifluoromethylpyridine compounds represented by the formula (II) are produced by dissolving a β-trifluoromethylpyridine compound represented by the formula (III) in an inert diluent and chlorinating it in a liquid phase. On this occasion, the reaction can be accelerated by the presence of a radical generator or the irradiation with ultraviolet rays or visual rays. In general, chlorine gas, sulfuryl chloride or the like is used as a chlorinating agent and an organic solvent of a halogenated hydrocarbon such as carbon tetrachloride, trichloroethylene, tetrachloroethylene or tetrachlorodifluoroethane is used as the inert diluent. Examples of the radical generator include azobisnitrile compounds such as 2,2'-azobisisobutyronitrile and azobismethylbutyronitrile and benzoyl peroxide compounds such as benzoyl peroxide, O,O'-dichlorobenzoyl peroxide, and P,P'-dimethylbenzoyl peroxide.

The use amounts of the inert diluent and chlorine are not categorically determined as it depends on the difference in the other reaction conditions. However, the use amount per 1 mol of the β-tifluoromethylpyridine compound may be from 5 to 30 mol for the inert diluent and is from 0.5 to 7 mol for chlorine in terms of effective chlorine. Further, the radical generator is used in an amount of 0.01 to 5% by weight per the β-trifluoromethylpyridine compound. The reaction temperature is from 35 to 150° C. and the reaction time is from 6 to 24 hours.

Usually, a liquid mixture containing chloro β-trifluoromethylpyridine compounds is collected from the reaction apparatus. The liquid mixture generally contains 2,5-CTF, 2,3-CTF and 2,3,6-DCTF. When intermediate products which do not reach formation of chloro β-tifluoromethylpyridine compounds are contained in the liquid mixture, these intermediate products can be separated and recovered together with unreacted raw materials or inert diluent and can be recycled to the reaction zone.

Moreover, the above Reaction 2 can be conducted according to the description in JP-A-55-122762.

(Reaction 3) As shown in the following reaction formula, a chloro β-trichloromethylpyridine compound represented by the formula (IV) is allowed to react with anhydrous hydrogen fluoride in a vapor phase in the presence of a catalyst and an inert diluent in a reaction apparatus to produce chloro β-trifluoromethylpyridine compounds represented by the formula (II) and a liquid mixture containing chloro β-trifluoromethylpyridine compounds represented by the formula (II) is fractionated from the reaction apparatus by a distillation operation. The liquid mixture generally contains 2,5-CTF, 2,3-CTF, 2,3,6-DCTF, and the like.

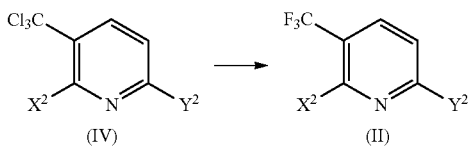

where $X^2$ and $Y^2$ are a hydrogen atom or a chlorine atom independently, provided that at least one of $X^2$ and $Y^2$ is a chlorine atom.

The above Reaction 3 is a reaction in which chloro β-trifluoromethylpyridine compounds represented by the formula (II) are produced by allowing a chloro β-trichloromethylpyridine compound represented by the formula (IV) to react with anhydrous hydrogen fluoride in a vapor phase in the presence of a catalyst and an inert diluent.

Examples of the catalyst used in the above Reaction 3 include metal fluorides and ammonium fluoride. Specific examples of metal fluorides include those the same as in the above Reaction 1. Specific examples of the ammonium fluoride include ammonium fluoride and acidic ammonium fluoride. Of the catalyst components, industrially, fluorides of chromium, iron, or nickel are desirable. Usually, the catalyst component is mixed with a carrier such as active carbon, active alumina or the like and molded into an appropriate-size particles or pellets, and then supplied to a reaction zone. The catalyst component may be directly supplied to a reaction tube in the form of a fluoride of the metal element and allowed to be present in the reaction zone. Or, the catalyst component may be allowed to be present in the reaction zone after the metal element is supplied to a reaction tube in the form of an oxide, a chloride, a hydroxide or a carbonate salt or in the form of a hydrate thereof, allowed to react with anhydrous hydrogen fluoride by allowing anhydrous hydrogen fluoride to pass through under high temperature, and converted into a desirable fluorine compound. For example, the reaction can be carried out after a molded product of an oxide or chloride of the above metal element, such as ferric chloride, chromium trioxide or nickel oxide supported on an alumina carrier is charged into a reaction tube, anhydrous hydrogen fluoride is introduced in advance, and they are allowed to react at 200 to 600° C. to convert the metal element into a fluoride.

At the time of carrying out the above Reaction 3, the raw material chloro β-trichloromethylpyridine compound and anhydrous hydrogen fluoride can be supplied separately or in a mixed state thereof into a reaction tube, or they may be supplied after mixed with the inert diluent. The raw materials may be vaporized and supplied as they are or the chloro β-trichloromethylpyridine compound may be once dissolved in the inert diluent and then vaporized and supplied. At the supply of the raw materials, in general, it is desirable to preheat them near to the boiling point of the chloro β-trichloromethylpyridine compound or the reaction temperature. As the inert diluent, inert solvents of halogenated hydrocarbons such as carbon tetrachloride, chloroform, methylene chloride, F-112 ($CFCl_2.CFCl_2$) and F-113 ($CF_2Cl.CFCl_2$) and inert gases such as nitrogen, argon, and helium are used. In the case of using the inert diluent, the use amount is not categorically determined but is from 1 to 20 mol, desirably from 3 to 10 mol per 1 mol of the chloro β-trichloromethylpyridine compound. The use amount of anhydrous hydrogen fluoride relative to the chloro β-trichloromethylpyridine compound is not categorically determined but is from 3 to 10 mol, desirably from 4 to 9 mol per 1 mol of the chloro β-trichloromethylpyridine compound. The use amount of the catalyst is not categorically determined but is the same as the use amount in the above Reaction 1.

Usually, in the reaction zone of the above Reaction 3, since the raw material chloro β-trichloromethylpyridine compound and anhydrous hydrogen fluoride, or the inert diluent are supplied at a constant flow rate, the solid matter of the catalyst forms a fluidized bed or a fixed bed. The reaction of the chloro β-trichloromethylpyridine compound with anhydrous hydrogen fluoride is carried out at 200 to 700° C., desirably at 300 to 500° C. The residence time of the reaction mixture in the reaction zone is from 1 to 20 seconds, desirably from 2 to 10 seconds.

From the reaction apparatus, after the aforementioned fluorination reaction, a gaseous reaction product is discharged. The gaseous reaction product contains a fluorinated product containing chloro β-trifluoromethylpyridine compounds as main components, unreacted hydrogen fluoride, hydrogen chloride as a by-product, and further the inert diluent. Through an appropriate cooling and condensing apparatus, the fluorinated product is liquefied to obtain a liquid mixture containing the chloro β-trifluoromethylpyridine compounds as main components. The liquid mixture generally contains 2,5-CTF, 2,3-CTF and 2,3,6-DCTF and the chloro β-trifluoromethylpyridine compounds are obtained, for example, in a yield of 80% or more based on the chloro β-trichloromethylpyridine compound. When intermediate products which do not reach formation of chloro β-trifluoromethylpyridine compounds are contained in the collected liquid mixture, the intermediate products can be separated and recovered together with unreacted raw materials or the inert diluent and can be recycled to the reaction zone.

Moreover, the above Reaction 3 can be conducted according to the description in JP-A-55-124762 and JP-A-56-100764.

(2) The liquid mixture fractionated in the above (1) contains about from 30 to 65% of 2,5-CTF, about from 5 to 20% of 2,3-CTF, and about from 10 to 30% of 2,3,6-DCTF. The proportions herein indicate peak area ratios based on gas chromatographic analysis.

From the above liquid mixture, a fraction mainly containing 2,5-CTF is fractionated by a distillation operation. At an industrial implementation scene, the operation is performed by fractionating a certain fraction in the process of producing the chloro β-trifluoromethylpyridine compounds by carrying out various reactions described in the above (1) and fractionating a liquid mixture containing the chloro β-trifluoromethylpyridine compounds by a distillation operation. The conditions of the distillation for fractionating the fraction mainly containing 2,5-CTF are not categorically determined, for example, in the case of performing in a distillation column, because the conditions in the vicinity of the column top and the vicinity of the column bottom are different owing to the influence of reflux, pressure loss and the like. However, in the conditions in the vicinity of the column bottom, the distillation can be performed at a temperature of from 90 to 130° C., desirably from 100 to 120° C. and under the condition of from 120 to 147 hPa, desirably from 127 to 140 hPa for about 5 to 15 hours. In the case of performing the distillation under normal pressure, it is performed at a temperature of usually from 130 to 160° C. as a condition in the vicinity of the column bottom. The fractionation of the fraction mainly containing 2,5-CTF can be finished when the peak area ratio of 2,5-CTF becomes about from 98 to 100% when the obtained fraction is suitably sampled and analyzed on a gas chromatography.

(3) From the liquid residue (residual reaction mixture) after the fraction mainly containing 2,5-CTF is fractionated in the above (2), crystals containing 2,3-CTF are obtained by a crystallization operation.

In the operation, at an industrial implementation scene, after the fraction mainly containing 2,5-CTF is fractionated, the distillation operation is subsequently performed in the distillation operation described in the above (2). The conditions of the distillation are not categorically determined, for example, in the case of performing in a distillation column, because the conditions in the vicinity of the column top and the vicinity of the column bottom are different owing to the influence of reflux, pressure loss and the like. However, in the conditions in the vicinity of the column bottom, the distillation can be performed at a temperature of from 110 to 130° C., desirably from 115 to 125° C. and under the condition of from 120 to 147 hPa, desirably from 127 to 140 hPa for about 1 to 5 hours. In the case of performing the distillation under normal pressure, it is performed at a temperature of usually from 160 to 180° C. as a condition in the vicinity of the column bottom. In the distillation, for example, a obtained fraction is suitably sampled and analyzed on a gas chromatography, and fractions after the peak area ratio of 2,3-CTF becomes about from 65 to 85% are collected.

From the fractions thus obtained, crystals containing 2,3-CTF are obtained by melt crystallization. The melt crystallization can be performed in the range where the liquid temperature is usually from 5 to 25° C., desirably from 10 to 20° C.

The obtained crystals are heated and melted and, at the time when the peak area ratio of 2,3-CTF exceeds 97.5% upon gas chromatographic analysis, the crystallization can be finished.

The crystallization can be performed using a crystallization apparatus known in the technical field and, for example, a continuous melt crystallization apparatus, a layered crystallization apparatus (thin film falling crystallization apparatus, static crystallization apparatus), a melt crystallization purification apparatus (composed of a combination of a scratching crystallization apparatus and a purification column), and the like can be used.

Specific examples of the melt crystallization apparatus which can be used in the present invention are not specifically limited but include a continuous melt crystallization apparatus that has a trade name KCP manufactured by Kureha Techno Engineering Co., Ltd. as an apparatus capable of continuous melt crystallization, a thin film semi-continuous melt crystallization apparatus of Sulzer Chemtech Ltd. as a semi-continuous melt crystallization apparatus, and a static batch melt crystallization apparatus of Sulzer Chemtech Ltd. as a batch-type melt crystallization apparatus. Other than these, known devices introduced in various catalogs and homepages can be used.

Moreover, the crystallization can be performed without using the crystallization apparatus as mentioned above. The specific method thereof includes a method of placing the above residual reaction mixture in a drum can, allowing it to stand at a liquid temperature ranging usually from 5 to 25° C., desirably from 10 to 20° C., i.e., about from 5 to 10° C. when defined by outside air temperature, for 5 to 24 hours, and subsequently discharging liquid matter from the drum can to obtain crystals containing 2,3-CTF. On this occasion, the liquid matter is easily discharged by tilting the drum can and the discharge operation can be made efficient by attaching a nozzle with a valve for discharging the liquid matter to the drum can.

(4) The purity of 2,3-CTF can be improved by heating and melting the crystals containing 2,3-CTF obtained in the above (3) to 40 to 60° C., desirably 45 to 55° C. and further performing a crystallization operation similar to the above one. In the present invention, the operation can be repeated until the purity of 2,3-CTF reaches desired one but the operation can be repeated at least twice, desirably twice to four times.

Various components in the method of the present invention can be appropriately selected from a plurality of aforementioned exemplifications and conditions and can be mutually combined. That is, the kinds, use forms, or use amounts of the compound (I), the catalyst and the inert diluent; temperatures of the distillation operation and the crystallization operation; standing time in the crystallization operation; the number of times of the crystallization operation; and the like can be appropriately selected from aforementioned usual ranges of exemplifications and conditions and preferable ranges of exemplifications and conditions and they can be mutually combined.

The following will list examples of preferable embodiments of the present invention but the invention should not be construed as being limited thereto.

[1] A method comprising:
  1) in the process of producing chloro β-trifluoromethylpyridine compounds by allowing a β-methylpyridine compound to react with chlorine and hydrogen fluoride in a reaction apparatus, allowing a β-trifluoromethylpyridine compound to react with chlorine in a reaction apparatus, or allowing a chloro β-trichloromethylpyridine compound to react with hydrogen fluoride in a reaction apparatus,
  2) fractionating a liquid mixture containing chloro β-trifluoromethylpyridine compounds from the reaction apparatus, and
  3) separating and purifying 2-chloro-3-trifluoromethylpyridine from the liquid mixture.

[2] The method according to the above [1], wherein the β-methylpyridine compound is represented by the formula (I):

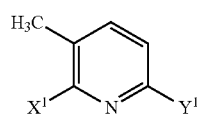

where $X^1$ and $Y^1$ are a hydrogen atom or a chlorine atom independently, the β-trifluoromethylpyridine compound is represented by the formula (III):

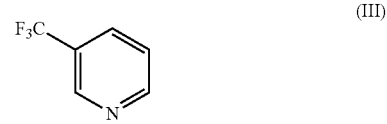

the chloro β-trichloromethylpyridine compound is represented by the formula (IV):

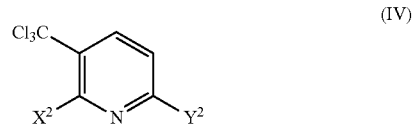

where $X^2$ and $Y^2$ are a hydrogen atom or a chlorine atom independently, provided that at least one of $X^2$ and $Y^2$ is a chlorine atom, and the chloro β-trifluoromethylpyridine compound is represented by the formula (II):

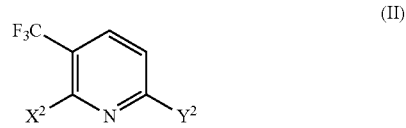

where $X^2$ and $Y^2$ are as mentioned above.

[3] The method according to the above [2] comprising:
  allowing the β-methylpyridine compound represented by the formula (I) to react with chlorine and anhydrous hydrogen fluoride in a vapor phase in the presence of a catalyst and an inert diluent in a reaction apparatus to produce the chloro β-trifluoromethylpyridine compound represented by the formula (II);
  allowing the β-trifluoromethylpyridine compound represented by the formula (III) to react with chlorine in a vapor or liquid phase in a reaction apparatus to produce the chloro β-trifluoromethylpyridine compound represented by the formula (II); or,
  allowing the chloro β-trichloromethylpyridine compound represented by the formula (IV) to react with anhydrous hydrogen fluoride in a vapor phase in the presence of a catalyst and an inert diluent in a reaction apparatus to produce the chloro β-trifluoromethylpyridine compound represented by the formula (II).

[4] The method according to the above [3] comprising:
  as a process of fractionating a liquid mixture containing chloro β-trifluoromethylpyridine compounds represented by the formula (II) from a reaction apparatus,
  fractionating 2-chloro-5-trifluoromethylpyridine by a distillation operation,
  further fractionating a liquid mixture containing 2-chloro-3-trifluoromethylpyridine by a distillation operation, and
  obtaining crystals containing 2-chloro-3-trifluoromethylpyridine from the liquid mixture by a crystallization operation.

[5] The method according to the above [4] comprising:
heating and melting the crystals containing 2-chloro-3-trifluoromethylpyridine obtained by the crystallization operation; and
further performing a crystallization operation.

[6] The method according to the above [4], wherein
the temperature of the reaction of the β-methylpyridine compound represented by the formula (I) with chlorine and anhydrous hydrogen fluoride is from 300 to 600° C.,
the temperature of the reaction of the β-trifluoromethylpyridine compound represented by the formula (III) with chlorine in a vapor phase is from 270 to 500° C.,
the temperature of the reaction of the β-trifluoromethylpyridine compound represented by the formula (III) with chlorine in a liquid phase is from 35 to 150° C., and
the temperature of the reaction of the chloro β-trichloromethylpyridine compound represented by the formula (IV) with anhydrous hydrogen fluoride is from 200 to 700° C.

[7] The method according to the above [4], wherein the temperature of the distillation operation for fractionating 2-chloro-5-trifluoromethylpyridine from the liquid mixture containing chloro β-trifluoromethylpyridine compounds represented by the formula (II) is from 90 to 130° C. under the condition of 120 to 147 hPa, and the temperature of the distillation operation for fractionating the liquid mixture containing 2-chloro-3-trifluoromethylpyridine is from 110 to 130° C. under the condition of 120 to 147 hPa.

[8] The method according to the above [4], comprising:
obtaining the crystals containing 2-chloro-3-trifluoromethylpyridine from the liquid mixture containing 2-chloro-3-trifluoromethylpyridine by the crystallization operation at a liquid temperature of 5 to 25° C.

EXAMPLES

The following will describe Examples of the present invention but the invention should not be construed as being limited thereto.

Example 1

(1) As a reaction apparatus, an Inconel-made vertical reaction tube having a catalyst fluidized bed whose reaction portion has an inner diameter of 97.1 mm and a height of 1,570 mm was installed, one obtained by connecting two Inconel-made preheating tubes having an inner diameter of 30 mm and a length of 1,000 mm was used for raw materials and an inert diluent, and the reaction tube and the preheating tubes were covered with an electric heater and a heat-insulating material so that temperature could be controlled.

One obtained by impregnating 2.2 kg of aluminum trifluoride having a particle diameter of 105 to 250 μm with 277 g of anhydrous ferric chloride was placed in the catalyst packing part and heated to 200° C., and anhydrous hydrogen fluoride was introduced at a rate of 2.3 L/minute for 1 hour to activate the catalyst.

After the reaction apparatus was heated to 400° C., β-picoline and nitrogen gas were introduced through the preheating tube so as to be rates of 6.8 g/minute and 9.9 L/minute, respectively, as a mixed gas of about 200° C. and chlorine gas, and anhydrous hydrogen fluoride were introduced through a preheating tube so as to be rates of 7.4 L/minute and 7.4 L/minute, respectively, as a mixed gas of about 200° C., and then they were allowed to react for about 30 hours. During the time, the activated catalyst was continuously supplied and discharged at a rate of 300 g/hour. The residence time of the reaction mixture in the tube was about 3.4 seconds.

A gas discharged from the reaction apparatus was allowed to pass through a water-washing column and an alkali-washing column to obtain a condensation product. Then, the condensation product was separated and neutralized with an aqueous ammonia solution to obtain 19.11 kg of an oily substance by steam distillation. By distilling the oily substance, 1.53 kg of a first fraction containing β-trifluoromethylpyridine as a main component and 9.56 kg of a main fraction containing 2-chloro-5-trifluoromethylpyridine (2,5-CTF) as a main component were fractionated. The residual fraction (post fraction) after the first fraction and the main fraction were fractionated contained 3.7% of 2-chloro-5-trifluoromethylpyridine (2,5-CTF), 14.5% of 2-chloro-3-trifluoromethylpyridine (2,3-CTF), 47.7% of 2,6-dichloro-3-trifluoromethylpyridine (2,3,6-DCTF), and 34.1% of others. The % designation herein is based on the peak area ratio (GCPA %) on gas chromatographic analysis.

(2) From the oily substance obtained in accordance with the method described in the above step (1), while a fraction containing 2-chloro-5-trifluoromethylpyridine (2,5-CTF) as a main component was fractionated by distillation, distillation was continued at 110 to 130° C. for the residual fraction. Upon sampling and gas chromatographic analysis, fractions after the peak area ratio of 2-chloro-3-trifluoromethylpyridine (2,3-CTF) exceeds 65% were collected. According to the operation method, about 2,400 kg of the above oily substance was distilled to obtain about 70 kg of a fraction in which the area value of 2-chloro-3-trifluoromethylpyridine (2,3-CTF) exceeded 65%.

(3) A fraction (liquid mixture) (284 kg) containing 2-chloro-3-trifluoromethylpyridine (2,3-CTF) obtained in accordance with the method described in the above step (2) was transferred to a drum can (200 L) and allowed to stand to crystallize 2-chloro-3-trifluoromethylpyridine (2,3-CTF). The melting point of 2,3-CTF is 37 to 39.5° C. After crystallization was performed under an air temperature lower than the melting point for 2 hours, a nozzle and a valve were attached to the discharge port of the drum can and the drum can was tilted sideway by a drum can tumbling device, and the liquid was received in a plastic bucket (50 L). After the crystals in the drum can was heated and melted and then again crystallized, the liquid was removed by the same operation as mentioned above to obtain 189 kg of crystals of 2,3-CTF (97.5% purity).

Example 2

A fraction (liquid mixture) (1,600 kg) containing 2-chloro-3-trifluoromethylpyridine (2,3-CTF) obtained in accordance with the method described in (1) and (2) of the above Example 1 was charged into a crystallization tank (200 L) and stirred at 40 to 60° C. for 30 minutes. The crystallization tank was cooled to 20 to 30° C. to crystallize 2-chloro-3-trifluoromethylpyridine (2,3-CTF). After crystal precipitation was confirmed, the whole was stirred at the same temperature for about one hour. After the stirring was finished, crystals were extracted from the bottom of the crystallization tank and the crystals were filtrated by a filtration machine (centrifuge) to obtain 528 kg of crystals of 2,3-CTF (97 to 99% purity).

Example 3

A fraction (liquid mixture) containing 2-chloro-3-trifluoromethylpyridine (2,3-CTF) obtained in accordance with the method described in the (1) and (2) of the above Example 1 is charged into a continuous melt crystallization apparatus (continuous melt crystallization apparatus having a trade name KCP manufactured by Kureha Techno Engineering Co., Ltd.). The liquid mixture is cooled to about 10° C. to crystallize 2,3-CTF for several hours. Under an environment capable of maintaining the temperature, a slurry containing 2,3-CTF as crystals is filtrated on a mesh-like filter plate. The obtained crystals containing 2,3-CTF as a main component are charged into a cylindrical vessel from the lower part and are pushed up to the upper part using a screw. A heating source capable of heating to 30 to 35° C. is present at the upper part and melts a liquid impurity included in or attached to the crystals to drop it to the lower part. Purification by heat exchange (Sweat method) in the vessel is performed by repeating the operation to obtain highly pure crystals of 2,3-CTF (97 to 99% purity). The liquid filtrated through the mesh-like filter plate is used as a raw material of the production step of the liquid mixture containing 2,3-CTF and the liquid extracted from the bottom of the cylindrical vessel is again used as a raw material of the melt crystallization.

Example 4

(1) As a reaction apparatus, a stainless steel-made reaction tube whose reaction part had an inner diameter of 42 mm and a length of 1,250 mm was used and a catalyst packing layer having a length of 250 mm was installed at a part 500 mm behind the inlet of the reaction tube.

On the other hand, as preheating parts, a stainless steel-made preheating tube having an inner diameter of 20 mm and a length of 500 mm was used for anhydrous hydrogen fluoride and chlorine, and a stainless steel-made preheating tube having an inner diameter of 20 mm and a length of 500 mm was used for β-picoline and carbon tetrachloride.

The reaction tube and the preheating tubes were covered with an electric heater and a heat-insulating material so that temperature could be externally controlled, and they were installed at a slant.

A blend of 0.03 mol of hydrated chromium trifluoride and 200 g of active alumina having a particle diameter of 4 to 6 mm was packed into the catalyst packing part of the reaction tube, and the reaction tube was heated to 430° C. and anhydrous hydrogen fluoride was allowed to pass through at a rate of 1 g/minute for 2 hours for activation. Thereafter, there were supplied 280 g (3 mol) of β-picoline and 2,310 g (15 mol) of carbon tetrachloride preheated to 230° C. and 960 g (13.5 mol) of chlorine and 480 g (24 mol) of anhydrous hydrogen fluoride preheated to 300° C. at an almost constant flow rate for 290 minutes to perform the reaction at 430° C. in a vapor phase. The residence time of the reaction mixture in the tube was about 9 seconds.

A gas discharged from the reaction tube was allowed to pass through a water-washing column and an alkali-washing column and condensed to obtain an oily substance. The oily substance was separated, collected, washed with water, and dried over sodium sulfate, and then carbon tetrachloride was distilled off under reduced pressure to obtain 420 g of an oily substance.

Using the finally obtained oily substance, distillation and crystallization are performed in accordance with (2) and (3) of the above Example 1 to obtain crystals of 2,3-CTF.

Example 5

After 300 g of γ-alumina was placed in the catalyst packing layer of the reaction tube used in the above Example 4 and activated with anhydrous hydrogen fluoride in the same manner as in the case of Example 4, 465 g (5 mol) of β-picoline and 3,850 g (25 mol) of carbon tetrachloride preheated to 250° C., and, 1,950 g (27.5 mol) of chlorine and 900 g (45 mol) of anhydrous hydrogen fluoride preheated to 300° C. at an almost constant flow rate for about 8 hours were supplied, and a vapor-phase reaction was carried out at a reaction temperature of 430° C. at a residence time of the reaction mixture of about 10.5 seconds.

A gas discharged from the reaction tube was treated in the same manner as in the case of Example 4 to obtain 708 g of an oily substance.

Using the obtained oily substance, distillation and crystallization are performed in accordance with (2) and (3) of the above Example 1 to obtain crystals of 2,3-CTF.

Example 6

A reaction was carried out in the same manner as in the case of Example 5 except that one obtained by supporting 0.1 mol of hydrated nickel(II) fluoride on 200 g of active carbon having a particle diameter of 2 to 4 mm was used instead of 300 g of γ-alumina and the activation of the alumina catalyst with anhydrous hydrogen fluoride was not performed, thereby obtaining 300 g of an oily substance.

Using the obtained oily substance, distillation and crystallization are performed in accordance with (2) and (3) of the above Example 1 to obtain crystals of 2,3-CTF.

Example 7

As a reaction apparatus, an Inconel-made vertical reaction tube having a catalyst fluidized bed whose reaction part has an inner diameter of 82 mm and a height of 1,100 mm was installed, one obtained by connecting two Inconel-made preheating tubes having an inner diameter of 8 mm and a length of 2,000 mm was used for raw materials and an inert diluent, and the reaction tube and the preheating tubes were covered with an electric heater and a heat-insulating material so that temperature could be controlled.

As a catalyst, 1.7 kg of the activated catalyst used in the above Example 4 which was pulverized and controlled to have a particle diameter of 0.18 to 0.4 mm was packed into the reaction part.

The reaction apparatus was heated to 430° C., β-picoline and nitrogen gas were introduced through the preheating tube so that the rates became 3.6 g/minute and 11.3 L/minute, respectively, as a mixed gas of about 200° C., and chlorine gas and anhydrous hydrogen fluoride were introduced through the preheating tube so that the rates became 2.8 L/minute and 2.5 L/minute, respectively, as a mixed gas of about 200° C. Then, they were allowed to react for about 5 hours. The residence time of the reaction mixture in the tube was about 7 seconds.

A gas discharged from the reaction apparatus was treated in the same manner as in the case of Example 4 to obtain 1,680 g of an oily substance.

Using the obtained oily substance, distillation and crystallization are performed in accordance with (2) and (3) of the above Example 1 to obtain crystals of 2,3-CTF.

Example 8

A reaction was carried out in the same manner as in the case of Example 7 for about 3 hours except that β-picoline, 3-trifluoromethylpyridine and nitrogen gas were supplied so that the rates became 2.38 g/minute, 1.88 g/minute and 11.3

L/minute, respectively, and chlorine gas and anhydrous hydrogen fluoride were supplied so that the rates became 2.8 L/minute and 2.5 L/minute, respectively. The residence time of the reaction mixture in the tube was about 7 seconds.

A gas discharged from the reaction apparatus was treated in the same manner as in the case of the above Example 4 to obtain 1,090 g of an oily substance.

Using the obtained oily substance, distillation and crystallization are performed in accordance with (2) and (3) of the above Example 1 to obtain crystals of 2,3-CTF.

Example 9

Using the same reaction apparatus as in the above Example 4, a catalyst obtained by supporting 0.1 mol of cobalt(II) fluoride on 200 g of active carbon having a particle diameter of 2 to 4 mm was placed in the catalyst packing part of the reaction tube. Thereafter, 280 g (3 mol) of β-picoline and 2,310 g (15 mol) of carbon tetrachloride preheated to 230° C., and, 960 g (13.5 mol) of chlorine and 480 g (24 mol) of anhydrous hydrogen fluoride preheated to 300° C. at an almost constant flow rate for 290 minutes were supplied, and a reaction was carried out at 430° C. in a vapor phase. The residence time of the reaction mixture in the tube was about 9 seconds.

A gas discharged from the reaction tube was allowed to pass through a water-washing column and an alkali-washing column and was condensed to obtain an oily substance. The oily substance was separated, collected, washed with water, and dried over sodium sulfate, and then carbon tetrachloride was distilled off under reduced pressure to obtain 280 g of an oily substance.

Using the finally obtained oily substance, distillation and crystallization are performed in accordance with (2) and (3) of the above Example 1 to obtain crystals of 2,3-CTF.

Example 10

An oily substance was obtained in an amount of 340 g in the same manner as in the above Example 9 except that the catalyst was changed to manganese(III) fluoride.

Using the obtained oily substance, distillation and crystallization are performed in accordance with (2) and (3) of the above Example 1 to obtain crystals of 2,3-CTF.

Example 11

A glass-made reaction tube having a diameter of 4 cm and a length of 70 cm, which was fitted with a thermocouple, was used. Two glass-made gas blowing tubes were inserted into the reaction tube through a preheating device. The reaction tube was covered with an electric heater and a heat-insulating material so that temperature could be externally controlled, and they were installed at a slant. One gas blowing tube was used for the introduction of a dried chlorine gas and another blowing tube was used for the introduction of a mixed gas obtained by heating and vaporizing a carbon tetrachloride solution of 3-trifluoromethylpyridine in a nitrogen gas stream. A receiver fitted with a cooling tube was installed at the outlet of the reaction tube, for collecting discharged gases. A solution in which the molar ratio of 3-trifluoromethylpyridine to carbon tetrachloride was 1/10, chlorine and nitrogen were supplied into the reaction tube at rates of 5.9 mL, 184 mL and 610 mL, respectively, per minute for 30 minutes, and thus a vapor-phase reaction was carried out at 400° C. The residence time of the gasses in the reaction tube was about 10 seconds. A liquid substance collected in the receiver was washed with a dilute aqueous solution of ammonia and then dried over sodium sulfate, and carbon tetrachloride was removed by distillation under reduced pressure to obtain 24.8 g of a yellow oily substance.

Using the obtained oily substance, distillation and crystallization are performed in accordance with (2) and (3) of the above Example 1 to obtain crystals of 2,3-CTF.

The invention claimed is:

1. A method of producing a chloro-β-trifluoromethylpyridine compound of formula (II) wherein one of $X^2$ and $Y^2$ is Cl and the other is H or Cl:

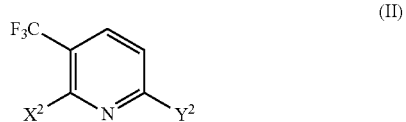

comprising:
1) reacting, in a reaction apparatus,
   a β-methylpyridine compound of formula (I) with chlorine and anhydrous HF in a vapor phase in the presence of a catalyst and an inert diluent,
   β-trifluoromethylpyridine of formula (III) with chlorine in a vapor or liquid phase, or
   a chloro-β-trichloromethylpyridine compound of formula (IV) with anhydrous HF in a vapor phase in the presence of a catalyst and an inert diluent,

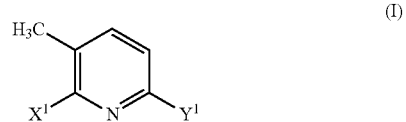

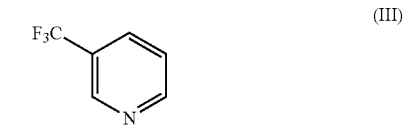

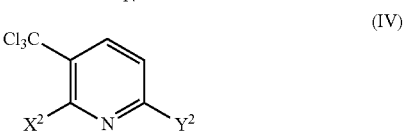

wherein $X^1$ and $Y^1$ each independently are H or Cl, and one of $X^2$ and $Y^2$ is Cl and the other is H or Cl;
2) fractionating a liquid mixture containing chloro-β-trifluoromethylpyridine compounds from the reaction apparatus, comprising
   2a) fractionating 2-chloro-5-trifluoromethylpyridine by distillation, and
   2b) further fractionating a liquid mixture containing 2-chloro-3-trifluoromethylpyridine by distillation, and
3) separating and purifying 2-chloro-3-trifluoromethylpyridine from the liquid mixture by crystallization,
wherein the catalyst comprises at least one selected from the group consisting of fluorides of chromium, fluorides of iron, fluorides of nickel, fluorides of manganese, fluorides of cobalt, fluorides of aluminum, fluorides of gamma-alumina and ammonium fluoride.

2. The method of claim 1 comprising heating and melting the crystals containing 2-chloro-3-trifluoromethylpyridine obtained by crystallization; and further performing crystallization.

3. The method of claim 1, wherein the temperature of the reaction
of the β-methylpyridine compound of formula (I) with chlorine and anhydrous HF is 300-600° C.,
of the β-trifluoromethylpyridine compound of formula (III) with chlorine in a vapor phase is 270-500° C.,
of the β-trifluoromethylpyridine compound of formula (III) with chlorine in a liquid phase is 35-150° C., and
of the chloro-β-trichloromethylpyridine compound of formula (IV) with anhydrous HF is 200-700° C.

4. The method of claim 1, wherein the temperature of the distillation is 90-130° C. in step 2a) and is 110-130° C. in step 2b), each under the condition of 120-147 hPa.

5. The method of claim 1, wherein the crystallization in step 3) is performed at a liquid temperature of 5-25° C.

\* \* \* \* \*